United States Patent [19]
Alden et al.

[11] Patent Number: 5,364,355
[45] Date of Patent: Nov. 15, 1994

[54] HOLDING SYSTEM FOR COILED INTRAVASCULAR PRODUCTS

[75] Inventors: Donald L. Alden, Sunnyvale; Isidro M. Gandionco, Fremont; Troy L. Thornton, Foster City; August R. Yambao, Fremont, all of Calif.

[73] Assignee: Advanced Cardiovascular Systems, Inc., Santa Clara, Calif.

[21] Appl. No.: 79,168

[22] Filed: Jun. 18, 1993

[51] Int. Cl.[5] .................. A61M 29/02; A44B 21/00
[52] U.S. Cl. ............................. 604/96; 606/194; 24/563; 24/543
[58] Field of Search .................. 604/96–102, 604/28; 24/489, 563, 543; 411/392, 424; 606/194; D8/356, 395, 396

[56] References Cited
U.S. PATENT DOCUMENTS

| | | | |
|---|---|---|---|
| D. 328,024 | 7/1992 | Grubicy et al. | D8/356 |
| 4,762,453 | 8/1988 | De Caro | 411/392 |
| 5,027,478 | 7/1991 | Suhr | D8/396 |

Primary Examiner—Jerome L. Kruter
Attorney, Agent, or Firm—Crosby, Heafey, Roach & May

[57] ABSTRACT

This invention is directed to a member which is mounted on an elongated intraluminal device such as a catheter or a guidewire, preferably the proximal portion thereof, which releasably holds at least one turn of a coiled product. The coiled product may be the intraluminal device on which the fixture is mounted or it may be a separate product. In one embodiment of the invention, the turn holding member has a body and at least one flexible arm which holds a turn against the body of the fixture. In another embodiment of the invention, the holding member is a tubular element having a wall portion with a spirally shaped cutout through which a turn of coiled product can be advanced into the inner lumen or the tubular element.

11 Claims, 2 Drawing Sheets

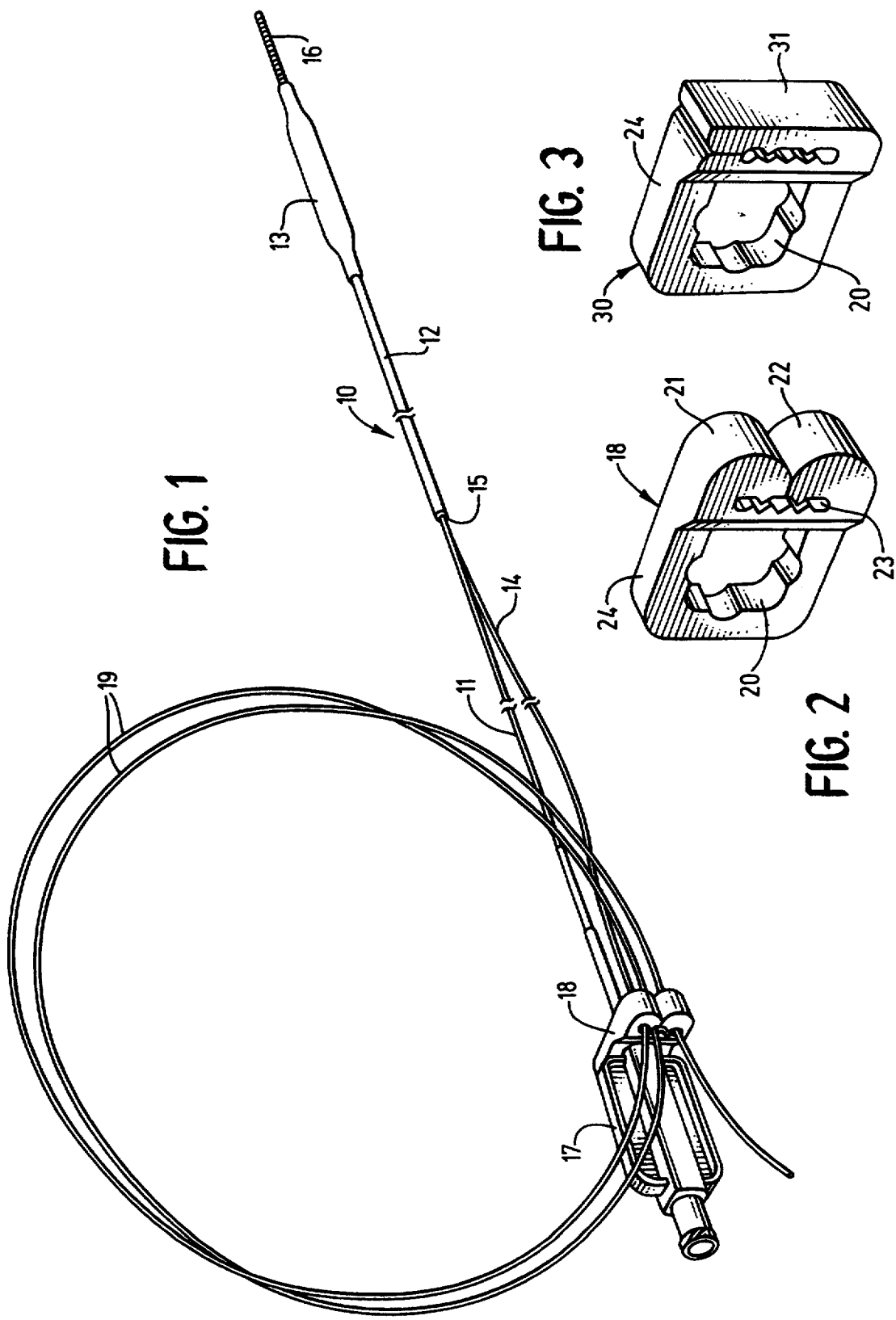

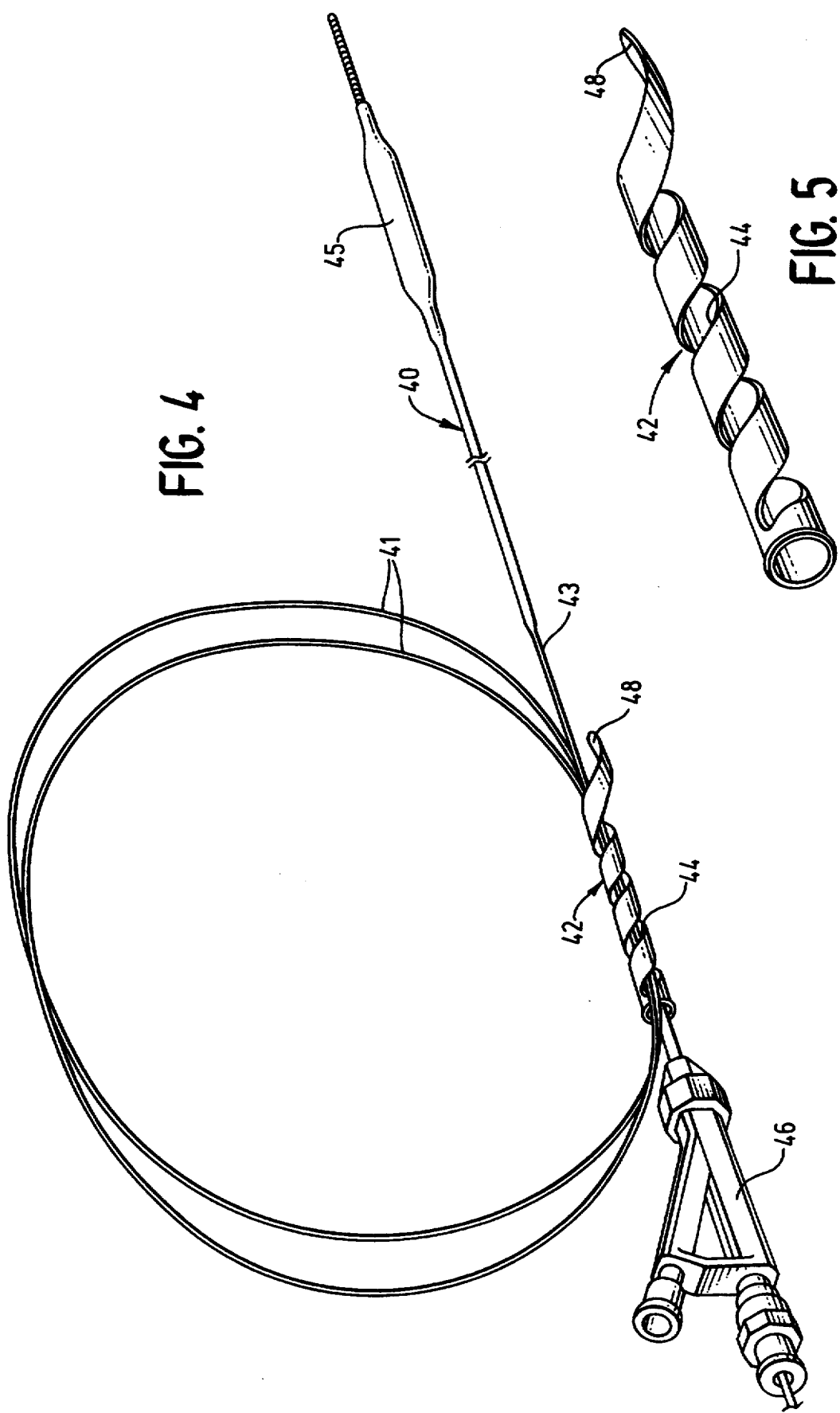

HOLDING SYSTEM FOR COILED INTRAVASCULAR PRODUCTS

BACKGROUND OF THE INVENTION

This invention generally relates to a system for holding flexible elongated articles in a coiled condition and particularly for sterile elongated articles such as dilatation catheters and guidewires for percutaneous transluminal coronary angioplasty (PTCA).

In PTCA procedures, a guiding catheter having a preshaped distal tip is percutaneously introduced into the cardiovascular system of a patient and advanced therein uptil the preshaped distal tip thereof is disposed within the aorta adjacent the ostium of the desired coronary artery. The guiding catheter is twisted or torqued from the proximal end to turn the distal tip of the guiding catheter so that it can be guided into the coronary ostium. A dilatation catheter having a balloon on the distal end thereof is introduced into and advanced through the guiding catheter to the distal tip thereof and then out of the distal tip of the guiding catheter until the balloon on the distal extremity of the dilatation catheter is properly positioned across the lesion. Once properly positioned, the flexible, relatively inelastic balloon tis inflated to a predetermined size with radiopaque liquid at relatively high pressures (e.g., 4–12 atmospheres) to dilate the stenosed region of the diseased artery. The balloon is then deflated so that the dilatation catheter can be removed from the dilated stenosis and blood flow can then be resumed therethrough. With over-the-wire and rapid exchange type dilatation catheters, they are advanced out of the guiding catheter over a previously positioned guidewire to the desired location within the patient's coronary anatomy. With fixed wire catheters the guiding member is fixed within the catheter so both are advanced together out the distal end of the guiding catheter to the desired location within the coronary arteries of the patient.

When a dilatation catheter or a guidewire is being manipulated during an angioplasty procedure, care must be exercised to ensure that the sterility of the catheter or the guidewire is not compromised by accidental contact with a non-sterile surface such as the floor or surrounding non-sterilized equipment. When not being used during the procedure, an unpackaged intravascular device, which can be over three feet long, usually must be placed in a sterile environment until it is used in the angioplasty procedure. This typically involves laying the catheter or the guidewire in an uncoiled condition over the draped surgical site on the patient. However, while the draped surgical site is sterile, it is not uncommon for the intravascular device to come into contact with a non-sterile surface due to all of the activity at the surgical site. Such contact with a non-sterile surface requires the contaminated intravascular device to be discarded and another sterilized intravascular device to be prepared for the angioplasty procedure. This replacement is expensive and inconvenient for the physician because a replacement catheter must also be vented to remove entrapped air and a replacement guidewire may need to have its distal extremity shaded.

Examples of instances during the angioplasty procedure in which an elongated dilatation catheter or guidewire can come into contact with a non-sterile surface requiring replacement of the compromised sterile product include when mounting a dilatation catheter onto a guidewire or withdrawing a dilatation catheter over a guidewire. Such intravascular devices also can come into contact with nonsterile surfaces when being stored for later use in a different artery.. The risk of non-sterile contact is particularly high when manipulating an assembled rapid exchange type dilatation catheter and a guidewire.

What has been needed and heretofore unavailable is a system which holds elongated intravascular devices in a relatively compact arrangement, particularly with sterilized devices, in order to minimize accidental contact with non-sterile surfaces. The present invention satisfies this and other needs.

SUMMARY OF THE INVENTION

This invention is directed to a system for holding flexible elongated products, particularly sterilized products, in a coiled arrangement to minimize the risk of undesirable contact with other surfaces.

The intraluminal system of the present invention generally includes an elongated, flexible, intraluminal device, such as a catheter or a guidewire, with means on the intraluminal device to releasably secure one or more turns of a coiled flexible product. The coiled flexible product may be a coiled portion of the intraluminal device on which the securing means is mounted or it may be a separate coiled product.

In one presently preferred embodiment the securing function is performed by means of one or more flexible arms on a body directly or indirectly secured to the intraluminal device so that when it is desired to remove the coiled product, it can be manually disengaged from the securing means without a .great deal of force. The securing means is adapted to hold at least one turn of an elongated coiled product and preferably a plurality of turns so that the coiled product can be maintained in a compact arrangement. However, the securing means is also adapted to readily release the coiled product. In this manner, the coiled product can be easily secured in the coiled condition on the intravascular device until the coiled product is needed for use.

In another presently preferred embodiment, the securing means is a tubular member which bas a wall with a spiral-shaped cutout adapted to receive a turn of a coiled flexible product. The turn of the coiled product is disposed within the tubular member through the spiral cutout by either wrapping the turn about the tubular member while pushing the turn through the cutout into the inner lumen of the tubular member or rotating the tubular member in the direction of the spiral cutout so that the turn of the coiled product will be pushed or otherwise advanced through the cutout into the inner lumen extending within the tubular member as the tubular member is being turned. The distal end of the tubular member deformed outwardly to ensure that the turn of the coiled product is more easily engaged when the tubular member is rotated to advance the turn into the inner lumen thereof.

These and other advantages of the invention will become more apparent from the following detailed description thereof when taken in conjunction with the accompanying exemplary, drawings.

BRIEF DESCRIPTION OF THE DRAWINGS

FIG. 1 is a perspective view cf a rapid exchange type dilatation catheter having means on the proximal end thereof to hold a coiled portion of the guidewire.

FIG. 2 is an enlarged perspective view of the means to secure a coiled product as shown in FIG. 1.

FIG. 3 is a perspective view of an alternative means to secure a coiled product.

FIG. 4 is a perspective view of a conventional over-the-wire type dilatation catheter, having means on the proximal end thereof to hold a coiled portion of the catheter.

FIG. 5 is an enlarged perspective view of the means to secure a coiled product as shown in FIG. 4.

DETAILED DESCRIPTION OF THE INVENTION

FIG. 1 illustrates a rapid exchange type dilatation catheter 10 which has a relatively stiff proximal section 11, a relatively flexible distal section 12, with the distal section being substantially shorter than the proximal section and a dilatation balloon 13 on the distal section. A guidewire 14 passes through an inner lumen (not shown) which extends from a proximal port 15 to a distal port 16 in the distal end of the distal section in a conventional rapid exchange fashion. An adapter 17 is secured to the proximal end of the proximal section 11 and is adapted to direct inflation fluid into and through an inner lumen (not shown) which is in fluid communication with the interior of the balloon 13.

Fixture 18 is provided on the distal end of the adapter 17 which will releasably hold a plurality of turns 19 of the guidewire 14. The fixture 18, as shown in FIG. 2, has a passageway 20 which is dimensioned so as to form a relatively tight fit on the adapter 17. If desired the fixture 18 may be adhesively or otherwise suitably secured to the adapter 17. The fixture 18 has a pair of flexible arms 21 add 22 which hold the turns 19 of the guidewire 14 within the slit 23. The mating ends of the arms 21 and 22 are preferably slightly spaced away from each other to facilitate insertion of the turns 19. The interfaces of the arms 21 and 22 with the body 24 of the fixture 18 are preferably serrated as shown to ensure that the turns of the guidewire 14 are not accidently pulled out of the slit 23. However, the arms 21 and 22 are relatively flexible so the turns 19 can be readily removed manually when the physician wishes to use the product. While the coiled product shown in Fig. ! is the guidewire 14, the proximal section 11 of the catheter 10.

FIG. 3 illustrates an alternative embodiment of a fixture 30 which has a single arm 31 for releasably holding the turns 19.

FIG. 4 depicts a conventional over-the-wire dilatation catheter 40 which has a proximal portion thereof coiled into a plurality of turns 41 which are held in a tubular element 42 slidably mounted onto the shaft 43 of the catheter. The tubular element 42 is provided with a spiral shaped cutout 44 which is adapted to receive the turns 41 of the coiled proximal portion of the catheter 40. The catheter 40 is also provided with en inflatable dilatation balloon 45 on a distal portion thereof and an adapter 46 mounted on the proximal end of the catheter shaft 43 which facilitates the introduction of inflation fluid into an inner lumen (not shown) of the catheter to inflate the balloon.

To engage the turns 41 of the coiled portion of the catheter shaft 43 the tubular element 42 is advanced from a position proximal to the turns and is rotated clockwise (observing from a proximal axial location on the catheter shaft) so as to advance the turns through the spiral cutout into the inner lumen 47 of the tubular element. As shown, the distal end 48 of the tubular element 42 extends away from the axis thereof so as to more easily engage the turns 41 when the tubular element is initially rotated. Withdrawal of the turns 41 from the inner lumen 47 of the tubular element 42 involves merely the counterclockwise rotation of the tubular element 42.

The elements which hold the turns 19 and 41 can be made from a variety of plastic materials including polyethylene, polyurethane, polyvinyl chloride and the like. The catheters, guidewires and other elongated members on which the fixture of the invention can be employed may be formed of conventional materials and may be of conventional structure.

While the invention is described herein in terms of holding the coiled turns by means of a member on the proximal end of an elongated intraluminal device, those skilled in the art will recognize that the holding member may be positioned on any portion of the elongated intraluminal device and can be movable along the length thereof. Preferably, the holding member is mounted on a proximal portion of the catheter, guidewire or the like which extends out of the patient. Various modifications and improvements may also be made to the invention without departing from the scope thereof.

What is claimed is:

1. An elongated intravascular device comprising:
    a) a flexible elongated shaft having a distal portion which is configured to be advanced through a patient's vascular system and a proximal portion which extends out of the patient when the distal portion is advanced through the patient's vascular system; and
    b) means secured on the proximal portion if the flexible elongated shaft to releasably secure at least one turn of a coiled elongated element to maintain a coiled structure.

2. The elongated intravascular device of claim 1 wherein the means to releasably secure at least one turn of a coiled elongated element is a fixture having a body portion and at least one flexible arm.

3. The elongated intravascular device of claim 2 wherein the fixture has a pair of inwardly directed arms element.

4. The elongated intravascular device of claim 2 wherein the fixture has a single arm for releasably securing at least one turn of the coiled elongated element.

5. The elongated intravascular device of claim 1 wherein the means to releasably secure at least one turn of a coiled elongated element comprises a tubular member with a wall having a spirally shaped cutout therein which is adapted to receive a turn of the coiled product.

6. The elongated intravascular device of claim 5 wherein the tubular member is slidably mounted on the elongated shaft thereof.

7. The intravascular device of claim 1 adapted to perform intravascular balloon dilatation which includes
    an inflation lumen extending within the flexible elongated shaft from the proximal section to the distal section thereof,
    an inflatable member on the distal portion of the catheter shaft having an interior in fluid communication with the inflation lumen, and
    means on the proximal portion to direct inflation fluid into the inflation lumen.

8. The intravascular device of claim 7 wherein the means to releasably secure at least one turn of a coiled product is a fixture having a body portion and at least one flexible arm adapted to secure a turn against the body portion.

9. The intravascular device of claim 7 wherein the fixture has a pair of inwardly directing arms.

10. The intravascular device of claim 7 wherein the means to releasably secure at least one turn of a coiled elongated element comprises a tubular member with a wall having a spirally shaped cutout therein which is adapted to receive a turn of the coiled elongated element.

11. The intravascular device of claim 7 wherein the tubular member is slidably mounted on the elongated shaft thereof.

* * * * *

UNITED STATES PATENT AND TRADEMARK OFFICE
CERTIFICATE OF CORRECTION

PATENT NO. : 5,364,355

DATED : November 15, 1994

INVENTOR(S) : Donald L. Alden et al.

It is certified that error appears in the above-identified patent and that said Letters Patent is hereby corrected as shown below:

Col. 4, claim 1, line 34, change "if" to --of--.

Signed and Sealed this

Fourteenth Day of March, 1995

Attest:

BRUCE LEHMAN

Attesting Officer

Commissioner of Patents and Trademarks